(12) United States Patent
Hillman et al.

(10) Patent No.: US 6,265,550 B1
(45) Date of Patent: Jul. 24, 2001

(54) INSULIN RECEPTOR TYROSINE KINASE SUBSTRATE

(75) Inventors: Jennifer L. Hillman, Mountain View; Preeti Lal; Purvi Shah, both of Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/270,117

(22) Filed: Mar. 15, 1999

Related U.S. Application Data

(62) Division of application No. 08/878,563, filed on Jun. 19, 1997, now Pat. No. 5,891,674.

(51) Int. Cl.⁷ .................................................. C07K 16/00
(52) U.S. Cl. ................................... 530/389.1; 530/387.1; 530/387.3; 530/388.1
(58) Field of Search ............................ 530/387.1, 387.3, 530/388.1, 387.9, 389.1; 435/194

(56) References Cited

PUBLICATIONS

Morrison, in Advances in Immunology 44:65–92, Academic Press, Inc., 1989.*

White, M.F. et al., "The Insulin Signaling System", *J. Biol. Chem.*, 269: 1–4 (1994).

Almind, K. et al., "A Common Amino Acid Polymorphism in Insulin Receptor Substrate–1 Causes Impaired Insulin Signaling", *J. Clin. Invest.*, 97: 2569–2575 (1996).

Yeh, T. et al., "Characterization and Cloning of a 58/53–kDa Substrate of the Insulin Receptor Tyrosine Kinase", *J. Biol. Chem.*, 271: 2921–2928 (1996) (GI 1203820).

Stoffel, M. et al., "Human insulin receptor substrate–1 gene (IRS1): chromosomal localization to 2q35–q36.1 and identification of a simple tandem repeat DNA polymorphism", *Diabetologia*, 36: 335–337 (1993).

Yeh, T.C. et al., (Direct Submission), GenBank Sequence Database (Accession 1203820), National Center for Biotechnology Information, National Library of Medicine, Bethesda, Maryland, 20894 (GI 1203820) Feb. 26, 1996.

Yeh, T.C. et al., (Direct Submission), GenBank Sequence Database (Accession U41899), National Center for Biotechnology Information, National Library of Medicine, Bethesda, Maryland, 20894 (GI 1203819; GI 1203820) Feb. 27, 1996.

Hillier et al., Accession No. R55195, The WashU–Merck EST project (May 22, 1995).

Marra et al., Accession No. AA061801 (The Marra M/Mouse EST Project) (Sep. 23, 1996).

Hillier et al., Accession No. AA235829, The WashU–Merck EST project (Mar. 6, 1997).

* cited by examiner

*Primary Examiner*—Yvonne Eyler
*Assistant Examiner*—Eliane Lazar-Wesley
(74) *Attorney, Agent, or Firm*—Incyte Genomics, Inc.

(57) ABSTRACT

The invention provides a human insulin receptor tyrosine kinase substrate (IRS-p53h) and polynucleotides which identify and encode IRS-p53h. The invention also provides expression vectors, host cells, agonists, antibodies and antagonists. The invention also provides methods for treating disorders associated with expression of IRS-p53h.

13 Claims, 9 Drawing Sheets

```
                                                                    9           18          27          36          45          54
                                                            5' GT CCG CTT TCG TCT CCG TCC TGC TGC CGT TAC CGC TGC CGC CGC TTG 63          72          81          90          99         108
                                                            CGT CCC CCG CTC CGG TCT GTG GTG CAG CCG GGA CCC AGG ACC ATG TCT TCT
                                                                                                                    M   S   S 117         126         135         144         153         162
                                                            CGC TCA GAG GAG ATG CAC CGG CTC ACG GAA AAT GTC TAT AAG ACC ATC ATG GAG
                                                             R   S   E   E   M   H   R   L   T   E   N   V   Y   K   T   I   M   E 171         180         189         198         207         216
                                                            CAG TTC AAC CCT AGC CTC CGG AAC TTC ATC GCC ATG GGG AAG AAT TAC GAG AAG
                                                             Q   F   N   P   S   L   R   N   F   I   A   M   G   K   N   Y   E   K 225         234         243         252         261         270
                                                            GCA CTG GCA GGT GTG ACG TAT GCA AAA GGC TAC TTT GAC GCC CTG GTG AAG
                                                             A   L   A   G   V   T   Y   A   K   G   Y   F   D   A   L   V   K 279         288         297         306         315         324
                                                            ATG GGG GAG CTG GCC AGC GAG AGC CAG GGC TCC AAA GAA CTC GGA GAC GTT CTC
                                                             M   G   E   L   A   S   E   S   Q   G   S   K   E   L   G   D   V   L 333         342         351         360         369         378
                                                            TTC CAG ATG GCT GAA GTC CAC AGG CAG ATC CAG AAT CAG CTG GAA GAA ATG CTG
                                                             F   Q   M   A   E   V   H   R   Q   I   Q   N   Q   L   E   E   M   L
```

FIG. 1A

```
        387             396     405     414     423     432
AAG TCT TTT CAC AAC GAG CTT ACG GAG CAG AAG GTG GAG CTG GAC
 K   S   F   H   N   E   L   T   Q   E   Q   K   V   E   L   D
        441             450     459     468     477     486
TCC AGG TAT CTG AGT GCT GCG CTA AAG TAC CAG ACT GAG CAA AGG AGC AAA
 S   R   Y   L   S   A   A   L   K   Y   Q   T   E   Q   R   S   K
        495             504     513     522     531     540
GGC GAC GCC CTG GAC AAG TGT CAG GCT GAG CTG CTG AAG CTT CGG AAG AAG AGC
 G   D   A   L   D   K   C   Q   A   E   L   L   K   L   R   K   K   S
        549             558     567     576     585     594
CAG AGC AAG AAT CCT CAG AAG TAC TCG GAC AAG GAG CTG CAG TAC ATC GAC
 Q   S   K   N   P   Q   K   Y   S   D   K   E   L   Q   Y   I   D
        603             612     621     630     639     648
GCC ATC AGC AAC AAG CAG GGC GAG CTG GAG AAT TAC GTG TCC GAC GGC TAC AAG
 A   I   S   N   K   Q   G   E   L   E   N   Y   V   S   D   G   Y   K
        657             666     675     684     693     702
ACC GCA CTG ACA GAG GAG TGC AGG CGC TTC TGC TTC CTG GTG GAG AAG CAG TGC
 T   A   L   T   E   E   C   R   R   F   C   F   L   V   E   K   Q   C
        711             720     729     738     747     756
GCC GTG GCC AAG AAC TCC GCG GCC TAC CAC TCC AAG GGC AAG GAG CTG CTG CCG
 A   V   A   K   N   S   A   A   Y   H   S   K   G   K   E   L   L   P
```

FIG. 1B

```
     765         774         783         792         801         810
CAG AAG CTG CCG CTG TGG CAA CAG GCC TGT GCC GAC CCC AGC AAG ATC CCG GAG
 Q   K   L   P   L   W   Q   Q   A   C   A   D   P   S   K   I   P   E 819         828         837         846         855         864
CGC GCG GTG CAG CTC ATG CAG CAG GTG GCC AGC AAC GGC GCC CTC CCC AGC AGC
 R   A   V   Q   L   M   Q   Q   V   A   S   N   G   A   L   P   S   S 873         882         891         900         909         918
GCC CTG TCG GCC TCC AAG TCC AAC CTG GTC ATT TCC GAC CCC ATT CCG GGG GCC
 A   L   S   A   S   K   S   N   L   V   I   S   D   P   I   P   G   A 927         936         945         954         963         972
AAG CCC CTG CCG GTG CCC GAG CCC GCA CTG GCA CCG TTC GTG GGG CGG ATG TCT GCC
 K   P   L   P   V   P   E   P   A   L   A   P   F   V   G   R   M   S   A 981         990         999         1008        1017        1026
CAG GAG AGC ACA CCC ATC ATG AAC GGC GTC ACA GGC CCG GAT GGC GAG GAC TAC
 Q   E   S   T   P   I   M   N   G   V   T   G   P   D   G   E   D   Y 1035        1044        1053        1062        1071        1080
AGC CCG TGG GCT GAC CGC AAG GCT GCC CAG CCC AAA TCC CTG TCT CCT CCG CAG
 S   P   W   A   D   R   K   A   A   Q   P   K   S   L   S   P   P   Q 1089        1098        1107        1116        1125        1134
TCT CAG AGC AAG CTC AGC GAC TCC TAC TCC AAC ACA CTC CCC GTG CGC AAG AGC
 S   Q   S   K   L   S   D   S   Y   S   N   T   L   P   V   R   K   S
```

FIG. 1C

```
        1143            1152            1161            1170            1179            1188
GTG ACC CCA AAA AAC AGC TAT GCC ACC GAG AAC AAG ACT CTG CCT CGC TCG
 V   T   P   K   N   S   Y   A   T   E   N   K   T   L   P   R   S 1197            1206            1215            1224            1233            1242
AGC TCC ATG GCA GCC GGC CTG GAG CGC AAT GGC CGT ATG CGG GTG AAG GCC ATC
 S   S   M   A   A   G   L   E   R   N   G   R   M   R   V   K   A   I 1251            1260            1269            1278            1287            1296
TTC TCC CAC GCT GCT GGG GAC AAC AGC ACC CTC CTG AGC TTC AAG GAG GGT GAC
 F   S   H   A   A   G   D   N   S   T   L   L   S   F   K   E   G   D 1305            1314            1323            1332            1341            1350
CTC ATT ACC CTG CTG GTG CCT GAG GCC CGC GAT GGC TGG CAC TAC GGA GAG AGT
 L   I   T   L   L   V   P   E   A   R   D   G   W   H   Y   G   E   S 1359            1368            1377            1386            1395            1404
GAG AAG ACC AAG ATG CGG GGC TGG TTT CCC TTC TCC TAC ACC CGG GTC TTG GAC
 E   K   T   K   M   R   G   W   F   P   F   S   Y   T   R   V   L   D 1413            1422            1431            1440            1449            1458
AGC GAT GGC AGT GAC AGG CTG CGC ATG AGC CTG CAG CAA GGG AAG AGC AGC AGC
 S   D   G   S   D   R   L   R   M   S   L   Q   Q   G   K   S   S   S 1467            1476            1485            1494            1503            1512
ACG GGC AAC CTC CTG GAC AAG GAC GAC CTG GCC AGC CCA CCC GAT TAC GGC
 T   G   N   L   L   D   K   D   D   L   A   S   P   P   D   Y   G
```

FIG. 1D

```
     1521           1530           1539          1548           1557           1566
GCC GCC TCC CGG GCT TTC CCC GCC CAG ACG GCC AGC GGC TTC AAG CAG AGG CCC
 A   A   S   R   A   F   P   A   Q   T   A   S   G   F   K   Q   R   P 1575           1584           1593          1602           1611           1620
TAC AGT GTG GCC GTG CCC GCC TTC TCC CAG GGC CTG GAT GAC TAT GGA GCG CGG
 Y   S   V   A   V   P   A   F   S   Q   G   L   D   D   Y   G   A   R 1629           1638           1647          1656           1665           1674
TCC ATG AGC AGG AAT CCC TTT GCC CAC GTC CAG AAG CTG AAG CCG ACA GTG ACC AAC
 S   M   S   R   N   P   F   A   H   V   Q   K   L   K   P   T   V   T   N 1683           1692           1701          1710           1719           1728
GAC AGG TCT GCC CCC CTC CTC AGC TGA TGG CCA CAT CTG CAG TGC TGC CCA TCT
 D   R   S   A   P   L   L   S 1737           1746           1755          1764           1773           1782
GGT GGC TTC CCC CGC CCT TCC CAT GTA GCC TGT TCT GTC ATC ATC TGT GCG TTC 1791           1800           1809          1818           1827           1836
CTG TGT AGA GAA CAT CCA GGC CCC GGC TGC CTG GTC TTG CCC CAC TTG AGT CTG 1845           1854           1863          1872           1881           1890
GCC TGG ACT GGA TTC CAG CTG TTC TAG GCA GGG CCG GGC AGA GTG GGG CGC AAG
```

FIG. 1E

```
1899      1908      1917      1926      1935      1944
CCC TGG ATG GCG AGA CCC AGT GGC TGG GNC TGC CAG GGC TGA GGG GGC GCT CTT 1953      1962      1971      1980      1989      1998
GAA GGT ACA CGC TCT GGT CAC ATG GCA TGG AGC TTG GGT ACC CTG AGT AAG GGA 2007      2016      2025      2034      2043      2052
GAA TTT GGC CAC TGG TGG CTG GGA GGG AAC TTG TTG CCT GCT GCT CTC CTG CCT 2061      2070      2079
AAT AAA AAG CTC TCC TGC AAA AAA AAA AT 3'
```

FIG. 1F

| | | |
|---|---|---|
| 1 | M S L S R S E E M H R L T E N V Y K T I | 918158 |
| 1 | M S L S R S E E M H R L T E N V Y K T I | GI 1203820 |
| 21 | M E Q F N P S L R N F I A M G K N Y E K | 918158 |
| 21 | M E Q F N P S L R N F I A M G K N Y E K | GI 1203820 |
| 41 | A L A G V T Y A A K G Y F D A L V K M G | 918158 |
| 41 | A L A G V T F A A K G Y F D A L V K M G | GI 1203820 |
| 61 | E L A S E S Q G S K E L G D V L F Q M A | 918158 |
| 61 | E L A S E S Q G S K E L G D V L F Q M A | GI 1203820 |
| 81 | E V H R Q I Q N Q L E E M L K S F H N E | 918158 |
| 81 | E V H R Q I Q N Q L E E M L K S F H N E | GI 1203820 |
| 101 | L L T Q L E Q K V E L D S R Y L S A A L | 918158 |
| 101 | L L T Q L E Q K V E L D S R Y L S A A L | GI 1203820 |
| 121 | K K Y Q T E Q R S K G D A L D K C Q A E | 918158 |
| 121 | K K Y Q A E Q R S K G D A L D K C Q A E | GI 1203820 |
| 141 | L K K L R K K S Q G S K N P Q K Y S D K | 918158 |
| 141 | L K K L R K K S Q G S K N P Q K Y S D K | GI 1203820 |
| 161 | E L Q Y I D A I S N K Q G E L E N Y V S | 918158 |
| 161 | E L Q Y I D A I S N K Q G E L E N Y V S | GI 1203820 |
| 181 | D G Y K T A L T E E C R R F C F L V E K | 918158 |
| 181 | D G Y K T A L T E E R R R F C F L V E K | GI 1203820 |
| 201 | Q C A V A K N S A A Y H S K G K E L L P | 918158 |
| 201 | Q C A V A K N S A A Y H S K G K E L L A | GI 1203820 |
| 221 | Q K L P L W Q Q A C A D P S K I P E R A | 918158 |
| 221 | Q K L P V W Q Q A C A D P N K I P D R A | GI 1203820 |

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 534 amino acids
      (B) TYPE: amino acid
      (C) STRANDEDNESS: single
      (D) TOPOLOGY: linear (vii) IMMEDIATE SOURCE:
      (A) LIBRARY: BRSTNOT04
      (B) CLONE: 918158

(xi) SEQUENCE DESCRIPTION: SEQ ID NO:1:

```
Met Ser Leu Ser Arg Ser Glu Glu Met His Arg Leu Thr Glu Asn Val
 1               5                  10                  15

Tyr Lys Thr Ile Met Glu Gln Phe Asn Pro Ser Leu Arg Asn Phe Ile
            20                  25                  30

Ala Met Gly Lys Asn Tyr Glu Lys Ala Leu Ala Gly Val Thr Tyr Ala
        35                  40                  45

Ala Lys Gly Tyr Phe Asp Ala Leu Val Lys Met Gly Glu Leu Ala Ser
    50                  55                  60

Glu Ser Gln Gly Ser Lys Glu Leu Gly Asp Val Leu Phe Gln Met Ala
65                  70                  75                  80

Glu Val His Arg Gln Ile Gln Asn Gln Leu Glu Glu Met Leu Lys Ser
                85                  90                  95

Phe His Asn Glu Leu Leu Thr Gln Leu Glu Gln Lys Val Glu Leu Asp
            100                 105                 110

Ser Arg Tyr Leu Ser Ala Ala Leu Lys Lys Tyr Gln Thr Glu Gln Arg
        115                 120                 125

Ser Lys Gly Asp Ala Leu Asp Lys Cys Gln Ala Glu Leu Lys Lys Leu
    130                 135                 140

Arg Lys Lys Ser Gln Gly Ser Lys Asn Pro Gln Lys Tyr Ser Asp Lys
```

```
145                 150                 155                 160
Glu Leu Gln Tyr Ile Asp Ala Ile Ser Asn Lys Gln Gly Glu Leu Glu
                165                 170                 175
Asn Tyr Val Ser Asp Gly Tyr Lys Thr Ala Leu Thr Glu Glu Cys Arg
            180                 185                 190
Arg Phe Cys Phe Leu Val Glu Lys Gln Cys Ala Val Ala Lys Asn Ser
        195                 200                 205
Ala Ala Tyr His Ser Lys Gly Lys Glu Leu Leu Pro Gln Lys Leu Pro
    210                 215                 220
Leu Trp Gln Gln Ala Cys Ala Asp Pro Ser Lys Ile Pro Glu Arg Ala
225                 230                 235                 240
Val Gln Leu Met Gln Gln Val Ala Ser Asn Gly Ala Thr Leu Pro Ser
                245                 250                 255
Ala Leu Ser Ala Ser Lys Ser Asn Leu Val Ile Ser Asp Pro Ile Pro
            260                 265                 270
Gly Ala Lys Pro Leu Pro Val Pro Pro Glu Leu Ala Pro Phe Val Gly
        275                 280                 285
Arg Met Ser Ala Gln Glu Ser Thr Pro Ile Met Asn Gly Val Thr Gly
    290                 295                 300
Pro Asp Gly Glu Asp Tyr Ser Pro Trp Ala Asp Arg Lys Ala Ala Gln
305                 310                 315                 320
Pro Lys Ser Leu Ser Pro Gln Ser Gln Ser Lys Leu Ser Asp Ser
                325                 330                 335
Tyr Ser Asn Thr Leu Pro Val Arg Lys Ser Val Thr Pro Lys Asn Ser
            340                 345                 350
Tyr Ala Thr Thr Glu Asn Lys Thr Leu Pro Arg Ser Ser Met Ala
        355                 360                 365
Ala Gly Leu Glu Arg Asn Gly Arg Met Arg Val Lys Ala Ile Phe Ser
    370                 375                 380
His Ala Ala Gly Asp Asn Ser Thr Leu Leu Ser Phe Lys Glu Gly Asp
385                 390                 395                 400
Leu Ile Thr Leu Leu Val Pro Glu Ala Arg Asp Gly Trp His Tyr Gly
                405                 410                 415
Glu Ser Glu Lys Thr Lys Met Arg Gly Trp Phe Pro Phe Ser Tyr Thr
            420                 425                 430
Arg Val Leu Asp Ser Asp Gly Ser Asp Arg Leu Arg Met Ser Leu Gln
        435                 440                 445
Gln Gly Lys Ser Ser Ser Thr Gly Asn Leu Leu Asp Lys Asp Asp Leu
    450                 455                 460
Ala Ser Pro Pro Asp Tyr Gly Ala Ala Ser Arg Ala Phe Pro Ala
465                 470                 475                 480
Gln Thr Ala Ser Gly Phe Lys Gln Arg Pro Tyr Ser Val Ala Val Pro
                485                 490                 495
Ala Phe Ser Gln Gly Leu Asp Asp Tyr Gly Ala Arg Ser Met Ser Arg
            500                 505                 510
Asn Pro Phe Ala His Val Gln Leu Lys Pro Thr Val Thr Asn Asp Arg
        515                 520                 525
Ser Ala Pro Leu Leu Ser
    530
```

(2) INFORMATION FOR SEQ ID NO:2:

(i) SEQUENCE CHARACTERISTICS:
        (A) LENGTH: 2080 base pairs (B) TYPE: nucleic acid
(C) STRANDEDNESS: single
(D) TOPOLOGY: linear (vii) IMMEDIATE SOURCE:
(A) LIBRARY: BRSTNOT04
(B) CLONE: 918158

(xi) SEQUENCE DESCRIPTION: SEQ ID NO:2:

```
GTCCGCTTTC GTCTCCGTCC TGCTGCCGTT ACCGCCGCTG CTGCCGCCGC TTGCGTCCCC      60
CGCTCCGGTC TGTGGTGCAG CCGGGACCCA GGACCATGTC TCTGTCTCGC TCAGAGGAGA     120
TGCACCGGCT CACGGAAAAT GTCTATAAGA CCATCATGGA GCAGTTCAAC CCTAGCCTCC     180
GGAACTTCAT CGCCATGGGG AAGAATTACG AGAAGGCACT GGCAGGTGTG ACGTATGCAG     240
CCAAAGGCTA CTTTGACGCC CTGGTGAAGA TGGGGGAGCT GGCCAGCGAG AGCCAGGGCT     300
CCAAAGAACT CGGAGACGTT CTCTTCCAGA TGGCTGAAGT CCACAGGCAG ATCCAGAATC     360
AGCTGGAAGA AATGCTGAAG TCTTTTCACA ACGAGCTGCT TACGCAGCTG GAGCAGAAGG     420
TGGAGCTGGA CTCCAGGTAT CTGAGTGCTG CGCTAAAGAA ATACCAGACT GAGCAAAGGA     480
GCAAAGGCGA CGCCCTGGAC AAGTGTCAGG CTGAGCTGAA GAAGCTTCGG AAGAAGAGCC     540
AGGGCAGCAA GAATCCTCAG AAGTACTCGG ACAAGGAGCT GCAGTACATC GACGCCATCA     600
GCAACAAGCA GGGCGAGCTG GAGAATTACG TGTCCGACGG CTACAAGACC GCACTGACAG     660
AGGAGTGCAG GCGCTTCTGC TTCCTGGTGG AGAAGCAGTG CGCCGTGGCC AAGAACTCCG     720
CGGCCTACCA CTCCAAGGGC AAGGAGCTGC TGCCGCAGAA GCTGCCGCTG TGGCAACAGG     780
CCTGTGCCGA CCCCAGCAAG ATCCCGGAGC GCGCGGTGCA GCTCATGCAG CAGGTGGCCA     840
GCAACGGCGC CACCCTCCCC AGCGCCCTGT CGGCCTCCAA GTCCAACCTG GTCATTTCCG     900
ACCCCATTCC GGGGGCCAAG CCCCTGCCGG TGCCCCCCGA GCTGGCACCG TTCGTGGGGC     960
GGATGTCTGC CCAGGAGAGC ACACCCATCA TGAACGGCGT CACAGGCCCG GATGGCGAGG    1020
ACTACAGCCC GTGGGCTGAC CGCAAGGCTG CCCAGCCCAA ATCCCTGTCT CCTCCGCAGT    1080
CTCAGAGCAA GCTCAGCGAC TCCTACTCCA ACACACTCCC CGTGCGCAAG AGCGTGACCC    1140
CAAAAAACAG CTATGCCACC ACCGAGAACA AGACTCTGCC TCGCTCGAGC TCCATGGCAG    1200
CCGGCCTGGA GCGCAATGGC CGTATGCGGG TGAAGGCCAT CTTCTCCCAC GCTGCTGGGG    1260
ACAACAGCAC CCTCCTGAGC TTCAAGGAGG GTGACCTCAT TACCCTGCTG GTGCCTGAGG    1320
CCCGCGATGG CTGGCACTAC GGAGAGAGTG AGAAGACCAA GATGCGGGGC TGGTTTCCCT    1380
TCTCCTACAC CCGGGTCTTG GACAGCGATG GCAGTGACAG GCTGCGCATG AGCCTGCAGC    1440
AAGGGAAGAG CAGCAGCACG GGCAACCTCC TGGACAAGGA CGACCTGGCC AGCCCACCCC    1500
CCGATTACGG CGCCGCCTCC CGGGCTTTCC CCGCCCAGAC GGCCAGCGGC TTCAAGCAGA    1560
GGCCCTACAG TGTGGCCGTG CCCGCCTTCT CCCAGGGCCT GGATGACTAT GGAGCGCGGT    1620
CCATGAGCAG GAATCCCTTT GCCCACGTCC AGCTGAAGCC GACAGTGACC AACGACAGGT    1680
CTGCCCCCCT CCTCAGCTGA TGGCCACATC TGCAGTGCTG CCCATCTGGT GGCTTCCCCC    1740
GCCCTTCCCA TGTAGCCTGT TCTGTCATCA TCTGTGCGTT CCTGTGTAGA GAACATCCAG    1800
GCCCCGGCTG CCTGGTCTTG CCCCACTTGA GTCTGGCCTG GACTGGATTC CAGCTGTTCT    1860
AGGCAGGGCC GGGCAGAGTG GGGCGCAAGC CCTGGATGGC GAGACCCAGT GGCTGGGNCT    1920
GCCAGGGCTG AGGGGCGCT CTTGAAGGTA CACGCTCTGG TCACATGGCA TGGAGCTTGG    1980
GTACCCTGAG TAAGGGAGAA TTTGGCCACT GGTGGCTGGG AGGGAACTTG TTGCCTGCTG    2040
CTCTCCTGCC TAATAAAAAG CTCTCCTGCA AAAAAAAAT                           2080
```

(2) INFORMATION FOR SEQ ID NO:3:

(i) SEQUENCE CHARACTERISTICS:
       (A) LENGTH: 521 amino acids
       (B) TYPE: amino acid
       (C) STRANDEDNESS: single
       (D) TOPOLOGY: linear (vii) IMMEDIATE SOURCE:
       (A) LIBRARY: GenBank
       (B) CLONE: 1203820

(xi) SEQUENCE DESCRIPTION: SEQ ID NO:3:

```
Met Ser Leu Ser Arg Ser Glu Glu Met His Arg Leu Thr Glu Asn Val
 1               5                  10                  15

Tyr Lys Thr Ile Met Glu Gln Phe Asn Pro Ser Leu Arg Asn Phe Ile
                20                  25                  30

Ala Met Gly Lys Asn Tyr Glu Lys Ala Leu Ala Gly Val Thr Phe Ala
            35                  40                  45

Ala Lys Gly Tyr Phe Asp Ala Leu Val Lys Met Gly Glu Leu Ala Ser
 50                  55                  60

Glu Ser Gln Gly Ser Lys Glu Leu Gly Asp Val Leu Phe Gln Met Ala
 65                  70                  75                  80

Glu Val His Arg Gln Ile Gln Asn Gln Leu Glu Met Leu Lys Ser
                85                  90                  95

Phe His Asn Glu Leu Leu Thr Gln Leu Glu Gln Lys Val Glu Leu Asp
               100                 105                 110

Ser Arg Tyr Leu Ser Ala Ala Leu Lys Lys Tyr Gln Ala Glu Gln Arg
               115                 120                 125

Ser Lys Gly Asp Ala Leu Asp Lys Cys Gln Ala Glu Leu Lys Lys Leu
 130                 135                 140

Arg Lys Lys Ser Gln Gly Ser Lys Asn Pro Gln Lys Tyr Ser Asp Lys
 145                 150                 155                 160

Glu Leu Gln Tyr Ile Asp Ala Ile Ser Asn Lys Gln Gly Glu Leu Glu
                165                 170                 175

Asn Tyr Val Ser Asp Gly Tyr Lys Thr Ala Leu Thr Glu Glu Arg Arg
                180                 185                 190

Arg Phe Cys Phe Leu Val Glu Lys Gln Cys Ala Val Ala Lys Asn Ser
                195                 200                 205

Ala Ala Tyr His Ser Lys Gly Lys Glu Leu Leu Ala Gln Lys Leu Pro
            210                 215                 220

Val Trp Gln Gln Ala Cys Ala Asp Pro Asn Lys Ile Pro Asp Arg Ala
225                 230                 235                 240

Val Gln Leu Met Gln Gln Ile Ala Ser Ser Asn Gly Ser Ile Leu Pro
                245                 250                 255

Ser Thr Leu Ser Ala Ser Lys Ser Asn Leu Val Ile Ser Asp Pro Ile
                260                 265                 270

Pro Gly Ala Lys Pro Leu Pro Val Pro Pro Glu Leu Ala Pro Phe Val
            275                 280                 285

Gly Arg Met Ser Ala Gln Glu Asn Val Pro Val Met Asn Gly Val Ala
            290                 295                 300

Gly Pro Asp Ser Glu Asp Tyr Asn Pro Trp Ala Asp Arg Lys Ala Ala
305                 310                 315                 320

Gln Pro Lys Ser Leu Ser Pro Gln Ser Gln Ser Lys Leu Ser Asp
            325                 330                 335
```

```
                                  -continued

Ser Tyr Ser Asn Thr Leu Pro Val Arg Lys Ser Val Thr Pro Lys Asn
            340                 345                 350

Ser Tyr Ala Thr Thr Glu Asn Lys Thr Leu Pro Arg Ser Ser Ser Met
            355                 360                 365

Ala Ala Gly Leu Glu Arg Asn Gly Arg Met Arg Val Lys Ala Ile Phe
    370                 375                 380

Ser His Ala Ala Gly Asp Asn Ser Thr Leu Leu Ser Phe Lys Glu Gly
385                 390                 395                 400

Asp Leu Ile Thr Leu Leu Val Pro Glu Ala Arg Asp Gly Trp His Tyr
            405                 410                 415

Gly Glu Ser Glu Lys Thr Lys Met Arg Gly Trp Phe Pro Phe Ser Tyr
            420                 425                 430

Thr Arg Val Leu Asp Ser Asp Gly Ser Asp Arg Leu His Met Ser Leu
            435                 440                 445

Gln Gln Gly Lys Ser Ser Thr Gly Asn Leu Leu Asp Lys Asp Asp
    450                 455                 460

Leu Ala Val Pro Pro Pro Asp Tyr Gly Thr Ser Ser Arg Ala Phe Pro
465                 470                 475                 480

Thr Gln Thr Ala Gly Thr Phe Lys Gln Arg Pro Tyr Ser Val Ala Val
            485                 490                 495

Pro Ala Phe Ser Gln Gly Leu Asp Asp Tyr Gly Ala Arg Ser Val Ser
            500                 505                 510

Ser Ala Asp Val Glu Val Ala Arg Phe
            515                 520
```

INSULIN RECEPTOR TYROSINE KINASE SUBSTRATE

This application is a divisional application of U.S. application Ser. No. 08/878,563, filed Jun. 19, 1997, now U.S. Pat. No. 5,891,674.

FIELD OF THE INVENTION

This invention relates to nucleic acid and amino acid sequences of a human insulin receptor tyrosine kinase substrate and to the use of these sequences in the diagnosis, prevention, and treatment of cancer, inflammation, and disorders associated with insulin response.

BACKGROUND OF THE INVENTION

Insulin controls blood glucose levels by stimulating glucose influx and metabolism in muscle and adipocytes and by inhibiting gluconeogenesis in the liver. Insulin also modifies the expression or the activity of a variety of enzymes and transport systems in nearly all cells.

Insulin action is mediated through the insulin receptor (IR), a transmembrane glycoprotein with protein tyrosine kinase (PTK) activity. Insulin binding triggers receptor autophosphorylation which activates PTK activity. The cellular response to insulin is mediated through tyrosine phosphorylation of cytosolic polypeptide substrates which act as second messengers in IR signal transduction. Once phosphorylated, the substrates bind to and activate various signal transduction proteins. The signal transduction proteins contain Src-homology-2 (SH2)-domains which bind phosphotyrosine-containing peptide motifs.

Several IR-PTK substrates have been described. The most extensively characterized substrate is the 185-kdal insulin receptor substrate-1 (IRS-1). IRS-1 is found in a variety of insulin responsive cells and tissues. It exhibits no intrinsic enzyme activity but, once phosphorylated, binds to and activates SH2-containing signal transduction proteins including phosphatidylinositol (PI) 3'-kinase and GRB-2, a regulator of the Ras pathway (White, M. F. et al. (1994) J. Biol. Chem. 269:1–4). Mutations in the IRS-1 gene impairs insulin-stimulated signaling and may contribute to insulin resistance in normal and diabetic populations (Almind, K. et al. (1996) J. Clin. Invest. 97:2569–2575).

Two 60-kdal protein substrates of the IR-PTK have been identified. One associates with the GTPase activator of Ras (termed GAP) and the other associates with PI 3'-kinase (Yeh, T. et al. (1996) J. Biol. Chem 271:2921–2928). Two additional substrates for IR-PTK with molecular masses of 53 and 58 kdal were recently identified in rodents. These proteins, p53 and p58, are closely related and may arise from alternative splicing of mRNA or differential post-translational modifications. P53 and p58 do not associate with GAP or PI 3'-kinase and are immunologically distinct from the 60-kDa GAP-associated protein and the 60-kDa PI 3'-kinase-associated protein (Yeh, et al., supra).

Post-receptor defects in the insulin signaling pathway are a common feature of type 2 (non-insulin-dependent) diabetes mellitus (Stoffel M. et al. (1993) Diabetologia 36: 335–337). Other disorders or conditions associated with disturbances in insulin response include hyperglycemia, myotonic muscular dystrophy, acanthosis nigricans, retinopathy, nephropathy, atherosclerotic coronary and peripheral arterial disease, and peripheral and autonomic neuropathies.

The discovery of a new human insulin receptor tyrosine kinase substrate and the polynucleotides encoding it satisfies a need in the art by providing new compositions which are useful in the diagnosis, prevention and treatment of cancer, inflammation, and disorders associated with insulin response.

SUMMARY OF THE INVENTION

The invention features a substantially purified polypeptide, human insulin receptor tyrosine kinase substrate (IRS-p53h), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding IRS-p53h under conditions suitable for the expression of the polypeptide; and b) recovering the polypeptide from the host cell culture.

The invention also provides a pharmaceutical composition comprising a substantially purified IRS-p53h having the amino acid sequence of SEQ ID NO:1 in conjunction with a suitable pharmaceutical carrier.

The invention also provides a purified antagonist which decreases the activity of a polypeptide of SEQ ID NO:1. In one aspect the invention provides a purified antibody which binds to a polypeptide comprising at least a fragment of the amino acid sequence of SEQ ID NO:1.

Still further, the invention provides a purified agonist which modulates the activity of the polypeptide of SEQ ID NO:1.

The invention also provides a method for treating or preventing a disorder associated with insulin response comprising administering to a subject in need of such treatment an effective amount of a pharmaceutical composition comprising purified IRS-p53h.

The invention also provides a method for treating or preventing cancer comprising administering to a subject in need of such treatment an effective amount of an antagonist to IRS-p53h.

The invention also provides a method for treating or preventing inflammation comprising administering to a subject in need of such treatment an effective amount of an antagonist to IRS-p53h.

The invention also provides a method for detecting a polynucleotide which encodes IRS-p53h in a biological sample comprising the steps of: a) hybridizing a polynucleotide sequence complementary to IRS-p53h (SEQ ID NO:1) to nucleic acid material of a biological sample, thereby forming a hybridization complex; and b) detecting the hybridization complex, wherein the presence of the complex correlates with the presence of a polynucleotide encoding IRS-p53h in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of IRS-p53h. The alignment was produced using MacDNASIS PRO software (Hitachi Software Engineering Co. Ltd. San Bruno, Calif.).

FIGS. 2A, 2B, and 2C show the amino acid sequence alignments between IRS-p53h (SEQ ID NO:1) and IRS p53 from hamster (GI 1203820; SEQ ID NO:3), produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

IRS-p53h, as used herein, refers to the amino acid sequences of substantially purified IRS-p53h obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to IRS-p53h, increases or prolongs the duration of the effect of IRS-p53h. Agonists may include proteins, nucleic acids, carbohydrates, or any other molecules which bind to and modulate the effect of IRS-p53h.

An "allele" or "allelic sequence", as used herein, is an alternative form of the gene encoding IRS-p53h. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding IRS-p53h as used herein include those with deletions, insertions, or substitutions of different nucleotides resulting in a polynucleotide that encodes the same or a functionally equivalent IRS-p53h. Included within this definition are polymorphisms which may or may not be readily detectable using a particular oligonucleotide probe of the polynucleotide encoding IRS-pS3h, and improper or unexpected hybridization to alleles, with a locus other than the normal chromosomal locus for the polynucleotide sequence encoding IRS-p53h. The encoded protein may also be "altered" and contain deletions, insertions, or substitutions of amino acid residues which produce a silent change and result in a functionally equivalent IRS-p53h. Deliberate amino acid substitutions may be made on the basis of similarity in polarity, charge, solubility, hydrophobicity, hydrophilicity, and/or the amphipathic nature of the residues as long as the biological or immunological activity of IRS-p53h is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of IRS-p53h are preferably about 5 to about 15 amino acids in length and retain the biological activity or the immunological activity of IRS-p53h. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to IRS-p53h, decreases the amount or the duration of the effect of the biological or immunological activity of IRS-p53h. Antagonists may include antibodies, proteins, nucleic acids, carbohydrates, or any other molecules which decrease the effect of IRS-p53h.

As used herein, the term "antibody" refers to intact molecules as well as fragments thereof, such as Fa, F(ab')$_2$, and Fv, which are capable of binding the epitopic determinant. Antibodies that bind IRS-p53h polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic IRS-p53h, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by basepairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding IRS-p53h (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding IRS-p53h in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to IRS-p53h or the encoded IRS-p53h. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of IRS-p53h. For example, modulation may cause an increase or a decrease in protein activity, binding characteristics, or any other biological, functional or immunological properties of IRS-p53h.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification, hybridization assays, or microarrays. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length IRS-p53h and fragments thereof.

The term "sample", as used herein, is used in its broadest sense. A biological sample suspected of containing nucleic acid encoding IRS-p53h, or fragments thereof, or IRS-p53h itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of IRS-p53h, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan.

Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human insulin receptor tyrosine kinase substrate (hereinafter referred to as "IRS-pS3h"), the polynucleotides encoding IRS-pS3h, and the use of these compositions for the diagnosis, prevention, or treatment of cancer, inflammation, and disorders associated with insulin response.

Nucleic acids encoding the IRS-p53h of the present invention were first identified in Incyte Clone 918158 from a carcinoma-associated breast tissue cDNA library (BRSTNOT04) using a computer search for amino acid sequence alignments. A consensus sequence, SEQ ID NO:2, was derived from the following overlapping and/or extended nucleic acid sequences: Incyte Clones 918158 (BRSTNOT04), 1342719 (COLNTUT03), and 1522281 (BLADTUT04).

In one embodiment, the invention encompasses a polypeptide comprising the amino acid sequence of SEQ ID NO:1, as shown in FIGS. 1A, 1B, 1C, 1D, 1E, and 1F. IRS-pS3h is 534 amino acids in length and contains numerous potential phosphorylation sites, including tyrosine kinase sites at residues Y 17, Y 115 and Y 178; a cAMP/cGMP-dependent protein kinase site at residue S 148; casein kinase II sites at residues S 4, T 19, T 103, S 129, S 158, S 291, T 303 and S 395; and protein kinase C sites at residues S 27, S 158, S 169, T 348, S 395, S 418, and S 440. As shown in FIGS. 2A, 2B, and 2C, IRS-p53h has chemical and structural homology with IRS p53 from hamster (GI 1203820; SEQ ID NO:3). In particular, IRS-p53h and hamster IRS p53 share 91% amino acid sequence identity. Northern analysis shows the expression of IRS-p53h in various tissues, most of which are immortalized or cancerous. Of particular note is the expression of IRS-p53h in cancers and cancer-associated tissues from adrenal gland, bladder, brain, breast, colon, esophagus, gall bladder, kidney, lung, pancreas, penis, paraganglion, prostate, and uterus; and in inflammation-associated tissues and cell lines including colon and small intestine (ulcerative colitis), gall bladder (cholecystitis), skin (erythema nodosum), synovium (rheumatoid arthritis), lymphocytes, and mononuclear cells.

The invention also encompasses IRS-p53h variants. A preferred IRS-p53h variant is one having at least 80%, and more preferably 90%, amino acid sequence identity to the IRS-p53h amino acid sequence (SEQ ID NO:1). A most preferred IRS-p53h variant is one having at least 95% amino acid sequence identity to SEQ ID NO:1.

The invention also encompasses polynucleotides which encode IRS-p53h. Accordingly, any nucleic acid sequence which encodes the amino acid sequence of IRS-p53h can be used to produce recombinant molecules which express IRS-p53h. In a particular embodiment, the invention encompasses the polynucleotide comprising the nucleic acid sequence of SEQ ID NO:2 as shown in FIGS. 1A, 1B, 1C, 1D, 1E, and 1F.

It will be appreciated by those skilled in the art that as a result of the degeneracy of the genetic code, a multitude of nucleotide sequences encoding IRS-p53h, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring IRS-p53h, and all such variations are to be considered as being specifically disclosed.

Although nucleotide sequences which encode IRS-p53h and its variants are preferably capable of hybridizing to the nucleotide sequence of the naturally occurring IRS-p53h under appropriately selected conditions of stringency, it may be advantageous to produce nucleotide sequences encoding IRS-p53h or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding IRS-p53h and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode IRS-p53h and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding IRS-p53h or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase DNA polymerase (US Biochemical Corp, Cleveland, Ohio.), Taq polymerase (Perkin Elmer), thermostable T7 polymerase (Amersham, Chicago, Ill.), or combinations of polymerases and proofreading exonucleases such as those found in the ELONGASE amplification system GIBCO/BRL (Gaithersburg, Md.). Preferably, the process is automated with machines such as the Hamilton Micro Lab 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding IRS-p53h may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR software, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode IRS-p53h may be used in recombinant DNA molecules to direct expression of IRS-p53h, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express IRS-p53h.

As will be understood by those of skill in the art, it may be advantageous to produce IRS-p53h-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter IRS-p53h encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding IRS-p53h may be ligated to a heterologous sequence to encode a fusion protein. For example, to screen peptide libraries for inhibitors of IRS-p53h activity, it may be useful to encode a chimeric IRS-p53h protein that can be recognized by a commercially available antibody. A fusion protein may also be engineered to contain a cleavage site located between the IRS-p53h encoding sequence and the heterologous protein sequence, so that IRS-pS3h may be cleaved and purified away from the heterologous moiety.

In another embodiment, sequences encoding IRS-p53h may be synthesized, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser. 7:225–232). Alternatively, the protein itself may be produced using chemical methods to synthesize the amino acid sequence of IRS-p53h, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of IRS-p53h, or any part thereof, may be altered during direct synthesis and/or combined using chemical methods with sequences from other proteins, or any part thereof, to produce a variant polypeptide.

In order to express a biologically active IRS-p53h, the nucleotide sequences encoding IRS-p53h or finctional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding IRS-p53h and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding IRS-p53h. These include, but are not limited to, microorganisms such as bacteria transformed with recombinant bacteriophage, plasmid, or cosmid DNA expression vectors; yeast transformed with yeast expression vectors; insect cell systems infected with S virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding IRS-p53h, vectors based on SV40 or EBV may be used with an appropriate selectable marker.

In bacterial systems, a number of expression vectors may be selected depending upon the use intended for IRS-p53h. For example, when large quantities of IRS-p53h are needed for the induction of antibodies, vectors which direct high level expression of fusion proteins that are readily purified may be used. Such vectors include, but are not limited to, the multifunctional *E. coli* cloning and expression vectors such as BLUESCRIPT phagemid (Stratagene), in which the sequence encoding IRS-p53h may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding IRS-p53h may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express IRS-p53h. For example, in one such system, *Autographa californica* nuclear polyhedrosis virus (AcNPV) is used as a vector to express foreign genes in *Spodoptera frugiperda* cells or in Trichoplusia larvae. The sequences encoding IRS-p53h may be cloned into a non-essential region of the virus, such as the polyhedrin gene, and placed under control of the polyhedrin promoter. Successful insertion of IRS-p53h will render the polyhedrin gene inactive and produce recombinant virus lacking coat protein. The recombinant viruses may then be used to infect, for example, *S. frugiperda* cells or Trichoplusia larvae in which IRS-p53h may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding IRS-p53h may be ligated into an adenovirus transcription/translation complex consisting of the late promoter and tripartite leader sequence. Insertion in a non-essential E1 or E3 region of the viral genome may be used to obtain a viable virus which is capable of expressing IRS-p53h in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding IRS-p53h. Such signals include the ATG initiation codon and adjacent sequences. In cases where sequences encoding IRS-p53h, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express IRS-p53h may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding IRS-p53h is inserted within a marker gene sequence, transformed cells containing sequences encoding IRS-p53h can be identified by the absence of marker gene function. Alternatively, a marker gene can be placed in tandem with a sequence encoding IRS-p53h under the control of a single promoter. Expression of the marker gene in response to induction or selection usually indicates expression of the tandem gene as well.

Alternatively, host cells which contain the nucleic acid sequence encoding IRS-p53h and express IRS-p53h may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding IRS-p53h can be detected by DNA-DNA or DNA-RNA hybridization or amplification using probes or fragments or fragments of polynucleotides encoding IRS-p53h. Nucleic acid amplification based assays involve the use of oligonucleotides or oligomers based on the sequences encoding IRS-p53h to detect transformants containing DNA or RNA encoding IRS-p53h.

A variety of protocols for detecting and measuring the expression of IRS-p53h, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on IRS-p53h is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding IRS-pS3h include oligolabeling, nick translation, end-labeling or PCR amplification using a labeled nucleotide. Alternatively, the sequences encoding IRS-p53h, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding IRS-p53h may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode IRS-p53h may be designed to contain signal sequences which direct secretion of IRS-p53h through a prokaryotic or eukaryotic cell membrane. Other constructions may be used to join sequences encoding IRS-p53h to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and IRS-p53h may be used to facilitate purification. One such expression vector provides for expression of a fusion protein containing IRS-p53h and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying IRS-p53h from the fusion protein. A discussion of vectors which contain fusion proteins is provided in Kroll, D. J. et al. (1993; DNA Cell Biol. 12:441–453).

In addition to recombinant production, fragments of IRS-p53h may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of IRS-p53h may be chemically synthesized separately and combined using chemical methods to produce the full length molecule.

THERAPEUTICS

Chemical and structural homology exits among IRS-p53h and IRS p53 from hamster (GI 1203820). In addition, IRS-p53h is expressed in cancers and in tissues associated with inflammation. Therefore, IRS-p53h appears to play a role in cancer, inflammation, and disorders associated with insulin response. In particular, increased expression or activity of IRS-p53h may be associated with cancer or inflammation, and decreased expression or activity of IRS-p53h may play a role in disorders associated with insulin response.

Therefore, in one embodiment, IRS-p53h or a fragment or derivative thereof may be administered to a subject to treat a disorder associated with insulin response. Such disorders include, but are not limited to, type 2 (non-insulin-dependent) diabetes mellitus, hyperglycemia, myotonic muscular dystrophy, acanthosis nigricans, retinopathy, nephropathy, atherosclerotic coronary and peripheral arterial disease, and peripheral and autonomic neuropathies.

In another embodiment, a vector capable of expressing IRS-p53h, or a fragment or a derivative thereof, may also be administered to a subject to treat a disorder associated with insulin response, including but not limited to those listed above.

In still another embodiment, an agonist of IRS-p53h may also be administered to a subject to treat a disorder associated with insulin response, including but not limited to those listed above.

In one embodiment, an antagonist of IRS-p53h may be administered to a subject to prevent or treat cancer. Such cancers include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind IRS-p53h may be used directly as an antagonist or indirectly as a targeting or delivery mechanism for bringing a pharmaceutical agent to cells or tissue which express IRS-p53h.

In another embodiment, a vector expressing the complement of the polynucleotide encoding IRS-p53h may be administered to a subject to treat or prevent cancer, including but not limited to the cancers listed above.

In one embodiment, an antagonist of IRS-p53h may be administered to a subject to prevent or treat inflammation of any type and, in particular, that which results from a particular disorder. Such disorders of inflammation include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, antibodies which specifically bind IRS-p53h may be used directly as an antagonist or indirectly as a targeting or delivery mechanism for bringing a pharmaceutical agent to cells or tissue which express IRS-p53h.

In another embodiment, a vector expressing the complement of the polynucleotide encoding IRS-p53h may be administered to a subject to treat or prevent inflammation of any type including but not limited to those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of IRS-p53h may be produced using methods which are generally known in the art. In particular, purified IRS-p53h may be used to produce antibodies or to screen libraries of pharmaceutical agents to identify those which specifically bind IRS-p53h.

Antibodies to IRS-p53h may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with IRS-p53h or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (*bacilli Calmette-Guerin*) and *Corynebacterium parvum* are especially preferable.

It is preferred that the oligopeptides, peptides, or fragments used to induce antibodies to IRS-p53h have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of IRS-p53h amino acids may be fused with those of another protein such as keyhole limpet hemocyanin and antibody produced against the chimeric molecule.

Monoclonal antibodies to IRS-p53h may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1 975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce IRS-p53h-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for IRS-p53h may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between IRS-p53h and its specific antibody. A two-site, monoclonal-based immunoassay utilizing monoclonal antibodies reactive to two non-interfering IRS-p53h epitopes is preferred, but a competitive binding assay may also be employed (Maddox, supra).

In another embodiment of the invention, the polynucleotides encoding IRS-p53h, or any fragment or complement thereof, may be used for therapeutic purposes. In one aspect, the complement of the polynucleotide encoding IRS-p53h may be used in situations in which it would be desirable to block the transcription of the mRNA. In particular, cells may be transformed with sequences complementary to polynucleotides encoding IRS-p53h. Thus, complementary molecules or fragments may be used to modulate IRS-p53h activity, or to achieve regulation of gene ftmction. Such technology is now well known in the art, and sense or antisense oligonucleotides or larger fragments, can be designed from various locations along the coding or control regions of sequences encoding IRS-p53h.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding IRS-p53h. These techniques are described both in Sambrook et al. (supra) and in Ausubel et al. (supra).

Genes encoding IRS-p53h can be turned off by transforming a cell or tissue with expression vectors which express high levels of a polynucleotide or fragment thereof which encodes IRS-p53h. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding IRS-p53h (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding IRS-p53h.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding IRS-p53h. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and a vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of IRS-p53h, antibodies to IRS-p53h, mimetics, agonists, antagonists, or inhibitors of IRS-p53h. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of IRS-p53h, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example IRS-p53h or fragments thereof, antibodies of IRS-p53h, agonists, antagonists or inhibitors of IRS-p53h, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind IRS-p53h may be used for the diagnosis of conditions or diseases characterized by expression of IRS-p53h, or in assays to monitor patients being treated with IRS-p53h, agonists, antagonists or inhibitors. The antibodies useful for diagnostic purposes may be prepared in the same manner as those described above for therapeutics. Diagnostic assays for IRS-p53h include methods which utilize the antibody and a label to detect IRS-p53h in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring IRS-p53h are known in the art and provide a basis for diagnosing altered or abnormal levels of IRS-p53h expression. Normal or standard values for IRS-p53h expression are established by combining body fluids or cell extracts taken from normal mammalian subjects, preferably human, with antibody to IRS-p53h under conditions suitable for complex formation The amount of standard complex formation may be quantified by various methods, but preferably by photometric, means. Quantities of IRS-p53h expressed in subject, control and disease, samples from biopsied tissues are compared with the standard values. Deviation between standard and subject values establishes the parameters for diagnosing disease.

In another embodiment of the invention, the polynucleotides encoding IRS-p53h may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of IRS-p53h may be correlated with disease. The diagnostic assay may be used to distinguish between absence, presence, and excess expression of IRS-p53h, and to monitor regulation of IRS-p53h levels during therapeutic intervention.

In one aspect, hybridization with PCR probes which are capable of detecting polynucleotide sequences, including genomic sequences, encoding IRS-p53h or closely related molecules, may be used to identify nucleic acid sequences which encode IRS-p53h. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding IRS-p53h, alleles, or related sequences.

Probes may also be used for the detection of related sequences, and should preferably contain at least 50% of the nucleotides from any of the IRS-p53h encoding sequences. The hybridization probes of the subject invention may be DNA or RNA and derived from the nucleotide sequence of SEQ ID NO:2 or from genomic sequence including promoter, enhancer elements, and introns of the naturally occurring IRS-p53h.

Means for producing specific hybridization probes for DNAs encoding IRS-p53h include the cloning of nucleic acid sequences encoding IRS-p53h or IRS-p53h derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidinibiotin coupling systems, and the like.

Polynucleotide sequences encoding IRS-p53h may be used for the diagnosis of conditions, disorders, or diseases which are associated with expression of IRS-p53h. Examples of such conditions or diseases include type 2 (non-insulin-dependent) diabetes mellitus, hyperglycemia, myotonic muscular dystrophy, acanthosis nigricans, retinopathy, nephropathy, atherosclerotic coronary and peripheral arterial disease, peripheral and autonomic neuropathies, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves'disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, autoimmune thyroiditis, complications of cancer, hemodialysis, extracorporeal circulation; viral, bacterial, fungal, parasitic, protozoal, and helminthic infections, trauma, adenocarcinoma, leukemia, lymphoma, melanoma, myeloma, sarcoma, and teratocarcinoma, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding IRS-p53h may be used in Southern or northern analysis, dot blot, or other membrane-based technologies; in PCR technologies; or in dipstick, pin, ELISA assays or microarrays utilizing fluids or tissues from patient biopsies to detect altered IRS-p53h expression. Such qualitative or quantitative methods are well known in the art.

In a particular aspect, the nucleotide sequences encoding IRS-p53h may be useful in assays that detect activation or induction of various cancers, particularly those mentioned above. The nucleotide sequences encoding IRS-p53h may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding IRS-p53h in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of IRS-p53h, a normal or standard profile for expression is established. This may be accomplished by combining body fluids or cell extracts taken from normal subjects, either animal or human, with a sequence, or a fragment thereof, which encodes IRS-p53h, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding IRS-p53h may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of IRS-p53h include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides derived from any of the polynucleotide sequences described herein may be used as targets in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc.

Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the full length sequence; or unique oligonucleotides selected from particular areas along the length of the sequence. In certain situations, it may be appropriate to use oligonucleotide pairs on the microarray. The "pairs" will consist of two strands which are identical except for one nucleotide, preferably in the center. The number of oligonucleotide pairs may range from 10–500 for a given sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligonucleotides may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode IRS-p53h may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial PI constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding IRS-p53h on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, IRS-p53h, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between IRS-p53h and the agent being tested, may be measured.

Another technique for drug screening which may be used provides for high throughput screening of compounds having suitable binding affinity to the protein of interest as described in published PCT application WO84/03564. In this method, as applied to IRS-p53h large numbers of different small test compounds are synthesized on a solid substrate, such as plastic pins or some other surface. The test compounds are reacted with IRS-p53h, or fragments thereof, and washed. Bound IRS-p53h is then detected by methods well known in the art. Purified IRS-p53h can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding IRS-p53h specifically compete with a test compound for binding IRS-p53h. In this manner, the antibodies can be used to detect the presence of any peptide which shares one or more antigenic determinants with IRS-p53h.

In additional embodiments, the nucleotide sequences which encode IRS-p53h may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

BRSTNOT04 cDNA Library Construction

The BRSTNOT04 cDNA library was constructed from microscopically normal breast tissue removed from a 62-year-old female during unilateral extended simple mastectomy following diagnosis of invasive grade 3 (of 4), nuclear grade 2 (of 3) mammary ductal carcinoma. The surgical margins were found negative for tumor. Also, a 0.4 cm focus of in-situ carcinoma was identified in the lower quadrant of the breast. Prior to surgery, the patient was diagnosed with benign hypertension, cerebrovascular disease, atherosclerosis, hyperlipidemia, and hematuria. The patient family history included liver cancer in a sibling.

The frozen tissue was homogenized and lysed using a Brinkmann POLYTRON HOMOGENIZER PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8–70M ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water, and DNase treated at 37° C. The RNA extraction and precipitation were repeated as before. The mRNA was then isolated with the OLIGOTEX kit (QIAGEN, Inc.; Chatsworth, Cailf.) and used to construct the cDNA library.

The mRNA was handled according to the recommended protocols in the SUPERSCRIPT Plasmid System (Cat. #18248-013; Gibco/BRL). BRSTNOT04 cDNAs were fractionated on a Sepharose CL4B column (Cat. #275105-01; Pharmacia Upjohn), and those cDNAs exceeding 400 bp were ligated into the PSPORT 1. The plasmid PSPORT plasmid was subsequently transformed into DH5a competent cells (Cat. #18258-012; Gibco/BRL).

II Isolation and Sequencing of cDNA Clones

Plasmid DNA was released from the cells and purified using the REAL PREP 96 well plasmid isolator kit (Catalog #26173; QIAGEN, Inc.). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975; J. Mol. Biol. 94:441f), using a Hamilton MICRO-LAB 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding IRS-p53h occurs. Abundance and percent abundance are also reported. Abundance directly reflects the number of times a particular transcript is represented in a cDNA library, and percent abundance is abundance divided by the total number of sequences examined in the cDNA library.

V Extension of IRS-p53h Encoding Polynucleotides

The nucleic acid sequence of the Incyte Clone 918158 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 primer analyses software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |

-continued

| | |
|---|---|
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA purification kit (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2×Carb. The following day, several colonies were randomly picked from each plate and cultured in 150 µl of liquid LB/2×Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Biosciences), labeled by combining 50 pmol of each oligomer and 250 μCi of [γ-$^{32}$P] adenosine triphosphate (Amersharn) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS membrane, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR autoradiography film (Kodak, Rochester, N.Y.) is exposed to the blots, in a Phosphoimager or the blots are placed PHOSPHOIMAGER cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the IRS-p53h-encoding sequence, or any part thereof, is used to decrease or inhibit expression of naturally occurring IRS-p53h. Although use of oligonucleotides comprising from about 15 to about 30 base-pairs is described, essentially the same procedure is used with smaller or larger sequence fragments. Appropriate oligonucleotides are designed using OLIGO 4.06 primer analysis software and the coding sequence of IRS-p53h, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the IRS-p53h-encoding transcript.

IX Expression of IRS-p53h

Expression of IRS-p53h is accomplished by subcloning the cDNAs into appropriate vectors and transforming the vectors into host cells. In this case, the cloning vector is also used to express IRS-p53h in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of IRS-p53h into the bacterial growth media which can be used directly in the following assay for activity.

X Demonstration of IRS-pS3h Activity

Human IR is expressed in and partially purified from chinese hamster ovary cells or rat hepatoma cells as described by Yeh, et al. (supra). IRS-p53h is incubated with the partially purified human IR in the presence of 1 μm insulin, 5 mM MgCl$_2$, 5 mM MnCl$_2$, 0.5 mM ATP in 20 mM HEPES pH 7.5, 0.1% TRITON X-100 for 20 min at 25° C. The incubations are subjected to SDS-PAGE electrophoresis (Sambrook, supra). Tyrosine-phosphorylated IRS-p53h is detected by western blotting (Sambrook, supra) using a horseradish peroxidase-conjugated anti-phosphotyrosine antibody such as RC20 (Transduction Laboratories; Lexington, Ky.) and the ECL detection system (Amersham).

XI Production of IRS-p53h Specific Antibodies

IRS-pS3h that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring IRS-p53h Using Specific Antibodies

Naturally occurring or recombinant IRS-p53h is substantially purified by immunoaffinity chromatography using antibodies specific for IRS-p53h. An immunoaffinity column is constructed by covalently coupling IRS-p53h antibody to an activated chromatographic resin, such as CNBr-activated SEPHAROSE (Pharmacia & Upjohn). After the coupling, the resin is blocked and washed according to the manufacturer's instructions.

Media containing IRS-p53h is passed over the immunoaffinity column, and the column is washed under conditions that allow the preferential absorbance of IRS-p53h (e.g., high ionic strength buffers in the presence of detergent). The column is eluted under conditions that disrupt antibody/IRS-p53h binding (eg, a buffer of pH 2–3 or a high concentration of a chaotrope, such as urea or thiocyanate ion), and IRS-p53h is collected.

XIII Identification of Molecules Which Interact with IRS-p53h

IRS-p53h or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled IRS-p53h, washed and any wells with labeled IRS-p53h complex are assayed. Data obtained using different concentrations of IRS-p53h are used to calculate values for the number, affinity, and association of IRS-p53h with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated antibody which specifically binds to a polypeptide comprising an amino acid sequence of SEQ ID NO:1.

2. A composition comprising an antibody of claim 1 in conjunction with a suitable pharmaceutical carrier.

3. A method of preparing a polyclonal antibody with the specificity of an antibody of claim 1 comprising:
   a) immunizing an animal with the polypeptide of SEQ ID NO:1 under conditions to elicit an antibody response;
   b) isolating animal antibodies; and
   c) screening the isolated antibodies with the polypeptide thereby identifying a polyclonal antibody binds specifically to the polypeptide of SEQ ID NO:1.

4. An antibody produced by a method of claim 3.

5. A composition comprising an antibody of claim 4 in conjunction with a suitable pharmaceutical carrier.

6. A method of making a monoclonal antibody with the specificity of an antibody of claim 1 comprising:
   a) immunizing an animal with the polypeptide of SEQ ID NO:1 under conditions to elicit an antibody response;
   b) isolating antibody producing cells from the animal;
   c) fusing the antibody producing cells with immortalized cells in culture to form monoclonal antibody-producing hybridoma cells;
   d) culturing the hybridoma cells; and
   e) isolating from the culture monoclonal antibodies which binds specifically to the polypeptide of SEQ ID NO:1.

7. A monoclonal antibody produced by a method of claim 6.

8. A composition comprising an antibody of claim 7 in conjunction with a suitable pharmaceutical carrier.

9. An antibody of claim 1, wherein the antibody is:
   a) a chimeric antibody;
   b) a single chain antibody;
   c) a Fab fragment; or
   d) a F(ab')$_2$ fragment.

10. An antibody of claim 9, wherein the antibody is produced by screening a Fab expression library.

11. An antibody of claim 1, wherein the antibody is produced by screening a recombinant immunoglobulin library.

12. A method for detecting a polypeptide of SEQ ID NO:1 in a sample comprising the steps of:
   a) combining an antibody of claim 1 with a sample under conditions to allow specific binding; and
   b) detecting specific binding, wherein specific binding indicates the presence of polypeptide of SEQ ID NO:1 in the sample.

13. A method of using an antibody to purify a polypeptide of SEQ ID NO:1 from a sample, the method comprising:
   a) combining an antibody of claim 1 with a sample under conditions to allow specific binding; and
   b) separating the antibody from the protein, thereby obtaining purified polypeptide of SEQ ID NO:1.

* * * * *